United States Patent [19]

Isogawa et al.

[11] 4,185,994
[45] Jan. 29, 1980

[54] HERBICIDAL COMPOUND

[75] Inventors: Takayuki Isogawa; Makoto Nagatomi; Shosuke Imamura, all of Tokyo, Japan

[73] Assignee: Hodogaya Chemical Company, Limited, Toyko, Japan

[21] Appl. No.: 865,417

[22] Filed: Dec. 29, 1977

[30] Foreign Application Priority Data

Feb. 2, 1977 [JP] Japan .................... 52-9769

[51] Int. Cl.$^2$ .................... A01N 9/20; C07C 103/28
[52] U.S. Cl. ........................ 71/118; 260/559 B
[58] Field of Search .................. 260/559 B; 71/118

[56] References Cited

U.S. PATENT DOCUMENTS

| | | | |
|---|---|---|---|
| 3,133,119 | 5/1964 | Nikawitz | 260/559 A |
| 3,414,400 | 12/1968 | Watanabe | 71/118 |
| 3,485,872 | 12/1969 | Kageyama et al. | 71/118 |
| 3,522,033 | 7/1970 | Kageyama et al. | 71/118 |
| 3,549,349 | 12/1970 | Gramlich | 71/118 |
| 3,714,252 | 1/1973 | Kiefer et al. | 260/562 A |

FOREIGN PATENT DOCUMENTS 1518436  3/1968  France .................... 260/559 B
40-18734  8/1965  Japan .................... 260/559 B

OTHER PUBLICATIONS

Chemical Abstract vol. 62, 1965, pp. 2190h–2191, Zaugg, "Selective Herbicidal Composition".
"The Herbidical Effect of Some Substituted Anilides," G. Matolesy & M. Hamran, 1964 p. 118.

*Primary Examiner*—Winston A. Douglas
*Assistant Examiner*—Raymond K. Covington
*Attorney, Agent, or Firm*—Oblon, Fisher, Spivak, McClelland & Maier

[57] ABSTRACT

Herbicidal compounds are the compounds having the formula

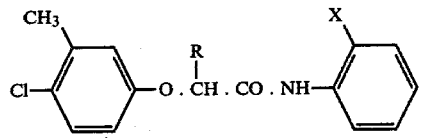

wherein R represents H or CH$_3$ and X represents H or Cl.

10 Claims, No Drawings

HERBICIDAL COMPOUND

BACKGROUND OF THE INVENTION

1. Field of the Invention

The present invention relates to herbicidal compounds. More particularly, it relates to herbicidal compounds having remarkably superior herbicidal effects.

2. Description of the Prior Arts

It has been known that phenoxyaliphatic acid derivatives such as 2,4-dichlorophenoxyacetic acid (2,4-D) and 2-methyl-4-chlorophenoxyacetic acid (MCP) cause serious phytotoxicity to rice plants to damage the yield when they are used as a soil treatment just before or after a transplantation of young rice plants. In order to overcome the phytotoxicity problem, various proposals have been made as disclosed in Japanese Patent Publication No. 24796/1970. However, they have not been satisfactory to overcome the disadvantages.

4-Chlorobenzyl-N,N-diethylthiolcarbamate and S-ethyl-N,N-hexamethylenthiolcarbamate are effective as the herbicide for barnyard grass and needle spikerush however they are substantially not effective as the herbicide for broadleaf weeds and perennial weeds such as arrowhead.

The inventors have studied to overcome the problem and have found special characteristics of the special compounds. The present invention has been completed by the findings.

SUMMARY OF THE INVENTION

It is an object of the present invention to provide a herbicidal compound having special characteristics of remarkably high herbicidal effect as the soil treatment agent in a paddy field or an up-land.

The foregoing and other objects of the present invention have been attained by providing a herbicidal compound having the formula

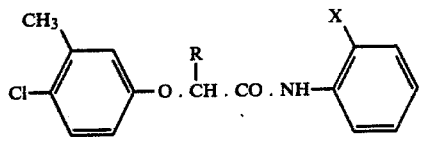

wherein R represents H or $CH_3$ and X represents H or Cl.

DETAILED DESCRIPTION OF THE PREFERRED EMBODIMENTS

The active ingredients of the present invention include the following compounds.

| Compound | Formula | Melting Point |
|---|---|---|
| 1 | (4-Cl, 3-CH₃-phenyl)-O.CH₂.CO.NH-(phenyl) | 107°~108° C. |
| 2 | (4-Cl, 3-CH₃-phenyl)-O.CH(CH₃).CO.NH-(phenyl) | 118°~120° C. |
| 3 | (4-Cl, 3-CH₃-phenyl)-O.CH₂.CO.NH-(2-Cl-phenyl) | 123°~125° C. |
| 4 | (4-Cl, 3-CH₃-phenyl)-O.CH(CH₃).CO.NH-(2-Cl-phenyl) | 96°~98° C. |

These compounds can be easily produced in high yield and high purity by reacting a phenoxycarboxylic chloride with an aniline.

These compounds can be blended to a suitable carrier to form an emulsifiable concentrate, a wettable powder, powder and granules. The liquid carriers are organic solvents and the solid carriers are fine mineral powder.

In the preparations of the compositions, suitable surfactants are combined so as to impart emulsifiable property, dispersing property and spreading property. These compounds can be used by combined with other agricultural chemical such as a fertilizer, herbicide, an insecticide and a fungicide.

The herbicidal compounds of the present invention are mainly to inhibit germination of weeds and they impart excellent germination inhibiting effect under flooded conditions.

It is possible to herbicide gramineous weeds such as barnyard grass and annual broadleaf weeds such as pickerel-weed, waterwort and rotala as well as perennial weeds such as needle spikerush, hardstem bulrush and arrowhead at the same time. Moreover, no phytotoxicity is found for the transplanted young rice plants even though about 4 times of the effective dose to substantially control the weeds at a rate of 200 g per 10 ares is applied.

The dose of the active ingredient is usually in a range of 20 to 400 g/10 ares preferably 50 to 300/10 ares, especially 100 to 200 g/10 ares.

The herbicidal compounds of the present invention can be applied for the soil treatment just before or after the transplantation of young rice plants to impart remarkably high selectivity and excellent herbicidal effect. the optimum condition as the herbicide can be attained.

The preparation of the herbicidal compounds of the present invention will be illustrated by certain examples.

PREPARATION 1

In a 100 ml round bottom flask equipped with a reflux condenser, 27 g of 3-methyl-4-chlorophenoxyacetic acid and 32 g of thionyl chloride were charged and a small amount of zeolite was added and the mixture was refluxed until completely dissolving the reaction product. After the reaction, excess of thionyl chloride, and dissolved hydrochloric acid gas and sulfur dioxide gas were removed by a rotary evaporator and the product was distilled to obtain 25.0 g of 3-methyl-4-chlorophenoxyacetic acid chloride. The distillation was carried out at 121° to 125° C. under the pressure of 7 to 8 mmHg. The yield was 80.1%.

PREPARATION 2

In a four necked flask equipped with a thermometer, a dropping funnel, a reflux condenser and a stirrer, 1.9 g of aniline and 10 ml of benzene were charged and a solution containing 2.2 g of 3-methyl-4-chlorophenoxyacetic acid chloride in 5 ml of benzene was added dropwise through the funnel at room temperature during about 30 minutes. After the reaction, the reaction mixture was moved into a 100 ml separating funnel and the organic phase was washed with a dilute hydrochloric acid and then, with a dilute alkaline aqueous solution and then with water to remove impurities and dried and then, benzene was recovered to obtain 2.6 g of 3-methyl-4-chlorophenoxyacetic acid anilide having a melting point of 107° to 108° C. The yield was 92.9%.

EXPERIMENT 1

In each Wagner pot having a diameter of 16 cm, paddy soil was filled. A paddy soil containing various paddy field weed seeds was covered as the surface layer and barnyard grass seeds and hardstem bulrush seeds were sowed, and water was filled under puddling and the depth of water was varied to 3 cm.

Three yound rice plants (two stands)(Koshihikari) at 2 to 2.5 leaf stage were transplanted per each pot three tubers of arrowhead were sowed in each pot. After 4 days from the transplantation, the specific amount of the active ingredient was applied into water. After 20 days from the treatment with the herbicidal compound, the herbicidal effects to various weeds and the phytotoxicity to rice plant were observed under the following rating.

| Herbicidal effect | | Phytotoxicity to rice | |
|---|---|---|---|
| 0 | no effect | — | no damage |
| 1 | control 0 to 30% | ± | quite low damage |
| 2 | control 30 to 50% | + | low damage |
| 3 | control 50 to 80% | ++ | middle damage |

-continued

| Herbicidal effect | | Phytotoxicity to rice | |
|---|---|---|---|
| 4 | control 80 to 100% | +++ | high damage |
| 5 | control 100% | ++++ | serious damage |
| | | X | dried out | bulrush: *Scirpus juncoides* Roxb.
F : arrowhead: *Sagittaria pygmaea* Miq.

The results are shown in Table 1.

Table 1

| Active Ingredient | Dose g/10 a | Phytotoxicity to rice | Herbicidal Effect | | | | | |
|---|---|---|---|---|---|---|---|---|
| | | | (A) | (B) | (C) | (D) | (E) | (F) |
| Compound 1 | 800 | — | 5 | 5 | 5 | 5 | 5 | 5 |
| | 400 | — | 5 | 5 | 5 | 5 | 5 | 5 |
| | 200 | — | 4 | 5 | 5 | 5 | 4 | 4 |
| | 100 | — | 3 | 5 | 5 | 5 | 3 | 3 |
| Compound 2 | 800 | — | 5 | 5 | 5 | 5 | 5 | 5 |
| | 400 | — | 5 | 5 | 5 | 5 | 5 | 5 |
| | 200 | — | 4 | 5 | 5 | 5 | 5 | 4 |
| | 100 | — | 3 | 5 | 5 | 5 | 4 | 3 |
| Compound 3 | 800 | — | 5 | 5 | 5 | 5 | 5 | 5 |
| | 400 | — | 5 | 5 | 5 | 5 | 5 | 5 |
| | 200 | — | 4 | 5 | 5 | 5 | 4 | 4 |
| | 100 | — | 3 | 5 | 5 | 5 | 3 | 3 |
| Compound 4 | 800 | — | 5 | 5 | 5 | 5 | 5 | 5 |
| | 400 | — | 5 | 5 | 5 | 5 | 5 | 5 |
| | 200 | — | 5 | 5 | 5 | 5 | 5 | 5 |
| | 100 | — | 4 | 5 | 5 | 5 | 5 | 4 |
| 2,4-D (Ref.) | 80 | ++++ | 5 | 5 | 5 | 5 | 5 | 5 |
| | 40 | +++ | 5 | 5 | 5 | 5 | 5 | 5 |
| | 20 | ++ | 4 | 5 | 5 | 5 | 4 | 4 |
| | 10 | + | 3 | 5 | 5 | 4 | 3 | 3 |
| EHMTC (Ref.) | 800 | — | 5 | 2 | 3 | 5 | 3 | 2 |
| | 400 | — | 5 | 1 | 2 | 4 | 1 | 0 |
| | 200 | — | 5 | 0 | 0 | 2 | 0 | 0 |
| | 100 | — | 5 | 0 | 0 | 1 | 0 | 0 |

Note:
2,4-D: Δ 2,4-dichlorophenoxyacetic acid
EHMTC: S-ethyl-N,N-hexamethylenethiolcarbamate
Weeds:
(A): barnyard grass: *Echinochloa crusgalli* L.
(B): pickerel-weed: *Monochoria vaginalis* (Burm. fil) Presl
(C): waterwort: *Elatine triandra* Schk.
(D): umbrella plant: *Cyperus difformis* Linn.
(E): hardstem bulrush: *Scirpus juncoides* Roxb.
(F): arrowhead: *Sagittaria pygmaea* Miq.

As shown in Table 1, the herbicidal compounds of the invention imparted remarkably high herbicidal effect to all kinds of weeds and phytotoxicity to rice was not found even though the herbicidal compounds were applied at a dose of 800 g per 10 ares. In comparison with the results of 2,4-D and EHMTC; remarkably high advantages of the herbicidal compounds as the paddy field soil treatment agent are shown from the viewpoints of the herbicidal effect and phytotoxicity.

EXPERIMENT 2

In each 100 ml Erlenmeyer flask, 50 ml of a diluted solution of the active ingredient was charged and two stands of young rice plant at 2.5 to 3 leaf stage (Nihonbare) was fixed with cotton so as to dip only roots into the solution and the flask was kept at 25° to 30° C. in a glass humidity chamber.

After 10 days from the treatment, the conditions of foliage and root of the rice plant were observed and number of new rooting and length of roots were measured and the new rooting control percent was calculated by comparing with that of non-treatment.

The rating in the observation correspond to the rating for the phytotoxicity. The results are shown in Table 2.

Table 2

| Active Ingredient | Concentration (ppm) | Observation foliage | Observation root | New rooting percent (%) Number of rootings | New rooting percent (%) Average length |
|---|---|---|---|---|---|
| Compound 1 | 100 | X | X | 0 | 0 |
| | 30 | ± | | 73 | 91 |
| | 10 | — | — | 100 | 100 |
| | 3 | — | — | 100 | 100 |
| | 1 | — | — | 100 | 100 |
| Compound 2 | 100 | X | X | 0 | 0 |
| | 30 | ± | | 86 | 97 |
| | 10 | — | — | 100 | 100 |
| | 3 | — | — | 100 | 100 |
| | 1 | — | — | 100 | 100 |
| Compound 3 | 100 | X | X | 0 | 0 |
| | 30 | + | — | 80 | 100 |
| | 10 | — | — | 100 | 100 |
| | 3 | — | — | 100 | 100 |
| | 1 | — | — | 100 | 100 |
| Compound 4 | 100 | | X | 0 | 0 |
| | 30 | — | — | 100 | 100 |
| | 10 | — | — | 100 | 100 |
| | 3 | — | — | 100 | 100 |
| | 1 | — | — | 100 | 100 |
| MCP (Ref.) | 100 | X | X | 0 | 0 |
| | 30 | X | X | 0 | 0 |
| | 10 | X | X | 0 | 0 |
| | 3 | | X | 0 | 0 |
| | 1 | — | | 20 | 5 |
| Non-treatment | 0 | — | — | 100 | 100 |

Note: MCP; 2-methyl-4-chlorophenoxyacetic acid

As shown in Table 2, even though the solution of the herbicidal compounds of the invention is directly absorbed through the root of rice plant, phytotoxicity was remarkably low. The fact shows remarkably high safety to rice plants.

EXPERIMENT 3:

Up-land soil treatment:

In each unglazed pot having a diameter of 11 cm, up-land soil was filled, a soil containing up-land weed seeds of crabgrass, pigweed and smart-weed was covered as a surface layer in a depth of 3 cm, and wheat, up-land rice seeds were sowed and a soil was covered in a depth of 2 cm. Next day, a diluted solution of the active ingredient was applied at a rate of 5 cc per one pot and the pot was kept at 25° to 30° C. in a glass high humidity chamber to grow it.

After 20 days from the treatment, the control effects of the active ingredients to weeds and the phytotoxicity to the wheat and rice plants were observed in accordance with the ratings of Experiment 1. The results are shown in Table 3.

Table 3

| Active Ingredient | Dose g/10a | Phyto-toxicity Wheat | Phyto-toxicity Rice | Herbicidal effect (G) | Herbicidal effect (H) | Herbicidal effect (Q) |
|---|---|---|---|---|---|---|
| Compound 1 | 800 | — | — | 5 | 5 | 5 |
| | 400 | — | — | 4 | 5 | 5 |
| | 200 | — | — | 1 | 4 | 4 |
| Compound 2 | 800 | — | — | 5 | 5 | 5 |
| | 400 | — | — | 5 | 5 | 5 |
| | 200 | — | — | 2 | 5 | 4 |
| Compound 3 | 800 | — | — | 5 | 5 | 5 |
| | 400 | — | — | 4 | 5 | 5 |
| | 200 | — | — | 0 | 4 | 4 |
| Compound 4 | 800 | — | — | 5 | 5 | 5 |
| | 400 | — | — | 3 | 5 | 5 |
| | 200 | — | — | 3 | 5 | 5 |
| DCMU (Ref.) | 80 | — | — | 4 | 5 | 5 |
| | 40 | — | — | 1 | 0 | 0 |
| | 20 | — | — | 0 | 0 | 0 |

Note: DCMU;
Weeds;
(G); Crabgrass *Digitaria adscendens*
(H); Pigweed *Amaranthus retroflexus*
(Q); Smart-weed *Poligonum blumei*

As shown in Table 3, no phytotoxicity to wheat and rice was not found even though the dose of the herbicidal compound of the invention was 800 g per 10 ares.

The germinations of main up-land weeds of crabgrass, pigweed and smart-grass were controlled by applying them at a dose of 400 g per 10 ares.

High herbicidal effect was imparted to bread-leaf weeds such as pigweed and smart-grass by applying at a dose of 200 g per 10 ares. Typical compositions of the present invention will be illustrated by certain examples.

| Composition 1 | Emulsifiable Concentrate |
|---|---|
| Compound 1 | 30 wt. parts |
| Xylene | 35 wt. parts |
| Isophorone | 25 wt. parts |
| Sorpol 800A | 10 wt. parts |

(Surfactant manufactured by Toho Chemical Co.)
(polyoxyethylenesorbitane alkylate polyoxyethylenealkylphenol polymer)
The components were mixed to obtain the emulsifiable concentrate.

| Composition 2 | Wettable powder |
|---|---|
| Compound 2 | 50 wt. parts |
| Kaolin clay | 45 wt. parts |
| Sorpol 5039 | 5 wt. parts |

(Surfactant manufactured by Toho Chemical Co.)
(polyoxyethylenealkylaryl sulfonate)
The components were mixed and pulverized to obtain the wettable powder.

The components were mixed and pulverized to obtain the wettable powder.

| Composition 3 | Granules |
|---|---|
| Compound 4 | 10 wt. parts |
| Bentonite | 40 wt. parts |
| Kaolin clay | 45 wt. parts |
| Calcium ligninesulfonate | 5 wt. parts |

The components were mixed and granulated to obtain the granules.

What is claimed is:

1. A herbicidal compound having the formula

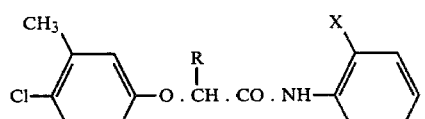

wherein R represent H or CH$_3$ and X represent H or Cl.

2. A herbicidal compound according to claim 1 which is 3-methyl-4-chlorophenoxyacetic acid anilide.

3. A herbicidal compound according to claim 1 which is 3-methyl-4-chlorophenoxyacetic acid 2-chloroanilide.

4. A hebicidal compound according to claim 1 which is 3-methyl-4-chlorophenoxy-i-propionic acid anilide.

5. A herbicidal compound according to claim 1 which is 3-methyl-4-chlorophenoxy-i-propionic acid-2-chloroanilide.

6. A method of treating soil with a herbicide, which comprises adding to the soil a compound of the formula (I)

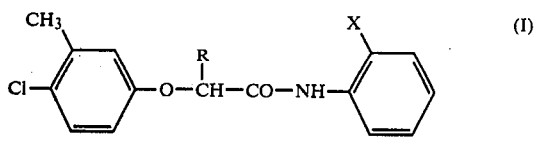

wherein R represents H or CH$_3$ and X represents H or Cl.

7. A method according to claim 6 wherein said compound is added in a range of 20 to 400 g/10 ares.

8. The method of claim 7 wherein said amount is 50–300 g/10 ares.

9. The method of claim 8 wherein said amount is 100 to 200 g/10 ares.

10. The method of claim 6 wherein said herbicide is added to the soil together with a suitable inert carrier.

* * * * *